(12) United States Patent
Yin

(10) Patent No.: US 8,445,521 B2
(45) Date of Patent: May 21, 2013

(54) SYNERGISTIC ANTIMICROBIAL COMPOSITION

(75) Inventor: Bei Yin, Buffalo Grove, IL (US)

(73) Assignee: Dow GLobal Technologies LLC, Midland, MI (US)

( * ) Notice: Subject to any disclaimer, the term of this patent is extended or adjusted under 35 U.S.C. 154(b) by 0 days.

(21) Appl. No.: 13/496,946

(22) PCT Filed: Sep. 15, 2010

(86) PCT No.: PCT/US2010/048845
§ 371 (c)(1),
(2), (4) Date: Mar. 19, 2012

(87) PCT Pub. No.: WO2011/037790
PCT Pub. Date: Mar. 31, 2011

(65) Prior Publication Data
US 2012/0184436 A1   Jul. 19, 2012

Related U.S. Application Data

(60) Provisional application No. 61/277,541, filed on Sep. 25, 2009.

(51) Int. Cl.
*A01N 31/08* (2006.01)
*A01N 31/02* (2006.01)
*A01N 33/20* (2006.01)
*A01N 43/76* (2006.01)
*A01P 1/00* (2006.01)

(52) U.S. Cl.
USPC ............ 514/374; 514/727; 514/736; 514/738

(58) Field of Classification Search
USPC .................................. 514/374, 727, 736, 738
See application file for complete search history.

(56) References Cited

U.S. PATENT DOCUMENTS

| 5,464,850 A * | 11/1995 | Voo et al. ....................... 514/372 |
| 7,262,222 B2 | 8/2007 | Carlson et al. |
| 2007/0203126 A1 | 8/2007 | Carlson et al. |

FOREIGN PATENT DOCUMENTS

JP    8-12505    *  1/1996

OTHER PUBLICATIONS

Roosmoore, H.W. et al., "Applications and mode of action of formaldehyde condensate biocides," Advances in applied microbiology, vol. 33, pp. 223-277 (Dec. 1998).*
Derwent abstract 1996-112576; abstracting JP 8-12505 (Jan. 1996).*

* cited by examiner

*Primary Examiner* — John Pak
(74) *Attorney, Agent, or Firm* — Kenneth Crimaldi

(57) ABSTRACT

A synergistic antimicrobial composition. The composition contains at least two components. The first component is ortho-phenylphenol or its alkali metal or ammonium salts. The second component is 4,4-dimethyloxazolidine (DMOZ).

5 Claims, No Drawings

SYNERGISTIC ANTIMICROBIAL COMPOSITION

This invention relates to combinations of biocides, the combinations having greater activity than would be observed for the individual antimicrobial compounds.

Use of combinations of at least two antimicrobial compounds can broaden potential markets, reduce use concentrations and costs, and reduce waste. In some cases, commercial antimicrobial compounds cannot provide effective control of microorganisms, even at high use concentrations, due to weak activity against certain types of microorganisms, or relatively slow antimicrobial action, or instability under certain conditions such as high temperature and high pH. Combinations of different antimicrobial compounds are sometimes used to provide overall control of microorganisms or to provide the same level of microbial control at lower use rates in a particular end use environment. For example, U.S. Pat. No. 7,262,222 discloses combinations of ortho-phenylphenol and a guanidine biocide or a quaternary ammonium biocide, but this reference does not suggest any of the combinations claimed herein. Moreover, there is a need for additional combinations of antimicrobial compounds having enhanced activity to provide effective control of microorganisms. The problem addressed by this invention is to provide such combinations of antimicrobial compounds.

STATEMENT OF THE INVENTION

The present invention is directed to a synergistic antimicrobial composition comprising: (a) ortho-phenylphenol or its alkali metal or ammonium salts; and (b) 4,4-dimethyloxazolidine (DMOZ); wherein a weight ratio of ortho-phenylphenol or its alkali metal or ammonium salts to 4,4-dimethyloxazolidine is from 4:1 to 1:15.

The present invention is further directed to a synergistic antimicrobial composition comprising: (a) ortho-phenylphenol or its alkali metal or ammonium salts; and (b) tris(hydroxymethyl)nitromethane (Tris Nitro); wherein a weight ratio of ortho-phenylphenol or its alkali metal or ammonium salts to tris(hydroxymethyl)nitromethane is from 15:1 to 1:15.

The present invention is further directed to a synergistic antimicrobial composition comprising: (a) ortho-phenylphenol or its alkali metal or ammonium salts; and (b) hexahydro-1,3,5-tris(2-hydroxyethyl)-s-triazine (HHT); wherein a weight ratio of ortho-phenylphenol or its alkali metal or ammonium salts to hexahydro-1,3,5-tris(2-hydroxyethyl)-s-triazine is from 15:1 to 1:15.

DETAILED DESCRIPTION OF THE INVENTION

As used herein, the following terms have the designated definitions, unless the context clearly indicates otherwise. The term "antimicrobial compound" refers to a compound capable of inhibiting the growth or propagation of microorganisms, and/or killing microorganisms; antimicrobial compounds include bactericides, bacteristats, fungicides, fungistats, algaecides and algistats, depending on the dose level applied, system conditions and the level of microbial control desired. The term "microorganism" includes, for example, fungi (such as yeast and mold), bacteria and algae. The following abbreviations are used throughout the specification: ppm=parts per million by weight (weight/weight), mL=milliliter, Unless otherwise specified, temperatures are in degrees centigrade (° C.), and references to percentages are by weight (wt %). Percentages of antimicrobial compounds in the composition of this invention are based on the total weight of active ingredients in the composition, i.e., the antimicrobial compounds themselves, exclusive of any amounts of solvents, carriers, dispersants, stabilizers or other materials which may be present. Ortho-phenylphenol or its alkali metal or ammonium salts includes lithium, sodium, potassium, rubidium, cesium and ammonium salts. If more than one form of ortho-phenylphenol is present, the biocide ratio is calculated from the total content of such compounds. In some embodiments of the invention, sodium o-phenylphenylate (NaOPP) is used.

In some embodiments of the invention, a weight ratio of the ortho-phenylphenol or its alkali metal or ammonium salts to 4,4-dimethyloxazolidine (DMOZ) is from 3:1 to 1:12, alternatively from 3:1 to 1:10, alternatively from 3:1 to 1:9, alternatively from 2:1 to 1:15, alternatively from 2:1 to 1:10, alternatively from 1:1 to 1:12, alternatively from 1:1 to 1:10, alternatively from 1:1 to 1:9.

In some embodiments of the invention, a weight ratio of the ortho-phenylphenol or its alkali metal or ammonium salts to tris(hydroxymethyl)nitromethane (Tris Nitro) is from 15:1 to 1:12, alternatively from 15:1 to 1:10, alternatively from 12:1 to 1:12, alternatively from 12:1 to 1:10, alternatively from 10:1 to 1:10, alternatively from 10:1 to 1:9, alternatively from 9:1 to 1:9.

In some embodiments of the invention, a weight ratio of the ortho-phenylphenol or its alkali metal or ammonium salts to hexahydro-1,3,5-tris(2-hydroxyethyl)-s-triazine is from 12:1 to 1:15, alternatively from 10:1 to 1:15, alternatively from 10:1 to 1:12, alternatively from 10:1 to 1:10, alternatively from 9:1 to 1:10, alternatively from 9:1 to 1:9.

In some embodiments of the invention, the antimicrobial combination of this invention is useful in oil and gas field injection, produced fluids, fracturing fluids and other functional fluids, oil and gas wells, oil and gas operation, separation, storage, and transportation systems, oil and gas pipelines, oil and gas vessels, and fuel. The combination is especially useful in aqueous fluids added to or produced by oil and gas well. The composition also is useful for controlling microorganisms in other industrial water and water containing/contaminated matrixes, such as cooling water, air washer, heat exchangers, boiler water, pulp and paper mill water, other industrial process water, ballast water, wastewater, metalworking fluids, latex, paint, coatings, adhesives, inks, tape joint compounds, pigment, water-based slurries, personal care and household products such as detergent, filtration systems (including reverse osmosis and ultrafiltration systems), toilet bowel, textiles, leather and leather production system, or a system used therewith.

Typically, the amount of the biocide combinations of the present invention to control the growth of microorganisms is from 10 ppm to 5,000 ppm active ingredient. In some embodiments of the invention, the active ingredients of the composition are present in an amount of at least 20 ppm, alternatively at least 50 ppm, alternatively at least 100 ppm, alternatively at least 150 ppm, alternatively at least 200 ppm. In some embodiments, the active ingredients of the composition are present in an amount of no more than 2,000 ppm, alternatively no more than 1,000 ppm, alternatively no more than 500 ppm, alternatively no more than 400 ppm, alternatively no more than 300 ppm, alternatively no more than 250 ppm, alternatively no more than 200 ppm, alternatively no more than 100 ppm, alternatively no more than 50 ppm. Concentrations mentioned above are in a liquid composition containing the biocide combinations. Biocide concentrations in a high-sulfide and high-temperature environment typically will be higher than in other environments.

The present invention also encompasses a method for reducing, or inhibiting, or preventing microbial growth in the use areas described above, especially in oil or natural gas production operations, by incorporating the claimed biocide combination into the materials.

EXAMPLES

Example 1

Synergistic Effect of NaOPP and DMOZ or Tris Nitro or HHT Against Sulfate Reducing Bacteria (SRB)

Inside an anaerobic chamber (BACTRON anaerobic chamber), a deaerated sterile salt solution (3.1183 g of NaCl, 1.3082 mg of NaHCO$_3$, 47.70 mg of KCl, 72.00 mg of CaCl$_2$, 54.49 mg of MgSO$_4$, 172.28 mg of Na$_2$SO$_4$, 43.92 mg of Na$_2$CO$_3$ in 1 L water) was contaminated with an oil field isolated anaerobic consortium, mainly SRB, at final bacterial concentrations of $10^6$ to $10^7$ CFU/mL. The aliquots of this contaminated water were then treated with NaOPP and DMOZ, or the NaOPP/DMOZ combination, NaOPP and Tris Nitro, or the NaOPP/Tris Nitro combination, NaOPP and HHT, or the NaOPP/HHT combination at different active concentration levels. After the mixtures were incubated at 40° C. for 24 hours, the biocidal efficacy was determined by minimum tested biocide concentration for complete bacterial kill in the aliquots (MBC). Tables 1-3 summarize the efficacy of each biocide and their blends, and the Synergy Index of each combination.

TABLE 1

Biocidal efficacy of NaOPP, DMOZ and NaOPP/DMOZ combination against anaerobic bacteria, and Synergy Index

| Ratio of NaOPP to DMOZ (active w/w) | MBC (active ppm) | | Synergy Index* |
|---|---|---|---|
| | NaOPP | DMOZ | |
| 1:0 | 333.3 | 0.0 | |
| 9:1 | 181.8 | 20.2 | 0.82 |
| 3:1 | 133.3 | 44.4 | 1.00 |
| 1:1 | 49.4 | 49.4 | 0.81 |
| 1:3 | 14.1 | 42.3 | 0.61 |
| 1:9 | 5.2 | 46.8 | 0.65 |
| 0:1 | 0.0 | 74.1 | |

*Synergy Index = Ca/CA + Cb/CB
Ca: Concentration of biocide A required to achieve complete bacterial kill when used in combination with biocide B
CA: Concentration of biocide A required to achieve complete bacterial kill when used alone
Cb: Concentration of biocide B required to achieve complete bacterial kill when used in combination with biocide A
CB: Concentration of biocide B required to achieve complete bacterial kill when used alone

TABLE 2

Biocidal efficacy of NaOPP, Tris Nitro and NaOPP/Tris Nitro combination against anaerobic bacteria, and Synergy Index

| Ratio of NaOPP to Tris Nitro (active w/w) | MBC (active ppm) | | Synergy Index |
|---|---|---|---|
| | NaOPP | Tris Nitro | |
| 1:0 | 500 | 0.0 | |
| 9:1 | 108.1 | 12.0 | 0.49 |
| 3:1 | 70.2 | 23.4 | 0.67 |
| 1:1 | 22.8 | 22.8 | 0.56 |
| 1:3 | 9.0 | 26.9 | 0.62 |
| 1:9 | 3.2 | 28.7 | 0.65 |
| 0:1 | 0.0 | 44.4 | |

TABLE 3

Biocidal efficacy of NaOPP, HHT and NaOPP/HHT combination against anaerobic bacteria, and Synergy Index

| Ratio of NaOPP to HHT (active w/w) | MBC (active ppm) | | Synergy Index |
|---|---|---|---|
| | NaOPP | HHT | |
| 1:0 | 500 | 0.0 | |
| 9:1 | 272.7 | 30.3 | 0.82 |
| 3:1 | 133.3 | 44.4 | 0.67 |
| 1:1 | 49.4 | 49.4 | 0.54 |
| 1:3 | 21.2 | 63.5 | 0.61 |
| 1:9 | 7.8 | 70.2 | 0.65 |
| 0:1 | 0.0 | 111.1 | |

Example 2

Synergistic Effect of NaOPP and DMOZ or Tris Nitro Against Aerobic Bacteria

A sterile NaCl solution (0.85%) was contaminated with *Pseudomonas aeruginosa*, ATCC 10145 and *Staphylococcus aureus*, ATCC 6538 at final bacterial concentration of ca. $10^6$ CFU/mL. The aliquots of this contaminated water were then treated with NaOPP and Tris Nitro, or the NaOPP/Tris Nitro combination, NaOPP and DMOZ or the NaOPP/DMOZ combination at different active concentration levels. After the mixtures were incubated at 37° C. for 24 hours, the biocidal efficacy was determined by minimum tested biocide concentration for complete bacteria kill in the aliquots. Tables 4 and 5 summarize the efficacy of each biocide and their blends, and the Synergy Index of each combination.

TABLE 4

Biocidal efficacy of NaOPP, DMOZ and NaOPP/DMOZ combination against aerobic bacteria, and Synergy Index

| Ratio of NaOPP to DMOZ (active w/w) | Average MBC (active ppm) | | Average Synergy Index | p value in ztest* |
|---|---|---|---|---|
| | NaOPP | DMOZ | | |
| 1:0 | 292.9 | 0.0 | | |
| 8.12:1 | 209.6 | 25.7 | 1.03 | 0.53 |
| 2.86:1 | 111.9 | 38.8 | 0.85 | 0.00 |
| 1:1 | 50.9 | 50.9 | 0.78 | 0.00 |
| 1:2.86 | 19.3 | 55.2 | 0.72 | 0.00 |
| 1:8.12 | 6.8 | 55.2 | 0.67 | 0.00 |
| 0:1 | 0.0 | 86.1 | | |

*P value < 0.05 means that there is significant difference between the average Synergy Index and 1.00

TABLE 5

Biocidal efficacy of NaOPP, Tris Nitro, and NaOPP/Tris Nitro combination against aerobic bacteria, and Synergy Index

| Ratio of NaOPP to Tris Nitro (active w/w) | MBC (active ppm) NaOPP | MBC (active ppm) Tris Nitro | Synergy Index |
|---|---|---|---|
| 1:0 | 266.3 | 0.0 | |
| 8.12:1 | 93.2 | 11.4 | 0.81 |
| 2.86:1 | 55.2 | 19.1 | 0.97 |
| 1:1 | <14.9 | <14.9 | <0.65 |
| 1:2.86 | <6.8 | <19.3 | <0.79 |
| 1:8.12 | <2.4 | <19.3 | <0.78 |
| 0:1 | 0.0 | 25.1 | |

The invention claimed is:

1. A synergistic antimicrobial composition comprising: (a) ortho-phenylphenol or its alkali metal or ammonium salts; and
   (b) 4,4-dimethyloxazolidine; wherein a weight ratio of ortho-phenylphenol or its alkali metal or ammonium salts to 4,4-dimethyloxazolidine is from 4:1 to 1:15.

2. The composition of claim 1 in which the weight ratio is from 3:1 to 1:10.

3. A synergistic antimicrobial composition comprising: (a) ortho-phenylphenol or its alkali metal or ammonium salts; and (b) tris(hydroxymethyl)nitromethane; wherein a weight ratio of ortho-phenylphenol or its alkali metal or ammonium salts to tris(hydroxymethyl)nitromethane is from 15:1 to 1:15.

4. The composition of claim 3 in which the weight ratio is from 12:1 to 1:12.

5. The composition of claim 4 in which the weight ratio is from 10:1 to 1:10.

* * * * *